(12) United States Patent
Odom et al.

(10) Patent No.: US 8,034,049 B2
(45) Date of Patent: Oct. 11, 2011

(54) SYSTEM AND METHOD FOR MEASURING INITIAL TISSUE IMPEDANCE

(75) Inventors: Darren Odom, Longmont, CO (US); Craig Weinberg, Denver, CO (US); Amy Denham, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1253 days.

(21) Appl. No.: 11/500,687

(22) Filed: Aug. 8, 2006

(65) Prior Publication Data

US 2008/0039831 A1 Feb. 14, 2008

(51) Int. Cl.
*A61B 18/18* (2006.01)
(52) U.S. Cl. .................. 606/34; 606/38; 606/42; 606/51
(58) Field of Classification Search .................. 606/34, 606/41, 38, 42, 50–52
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |

(Continued)

FOREIGN PATENT DOCUMENTS

DE 179607 3/1905

(Continued)

OTHER PUBLICATIONS

International Search Report EP 07008207.8; dated Sep. 5, 2007.

(Continued)

*Primary Examiner* — Roy Gibson

(57) ABSTRACT

An electrosurgical system and method are disclosed. The system includes an electrosurgical generator adapted to supply electrosurgical energy to tissue. The generator is further adapted to supply an electrical signal having at least one substantially constant value to tissue to determine initial tissue impedance response. The generator includes sensor circuitry adapted to continuously monitor initial tissue impedance response, wherein the initial tissue impedance response includes one of an initial impedance, an impedance drop, an impedance minimum and a first impedance rise. The generator also includes a microprocessor adapted to generate at least one tissue parameter based as a function of the initial impedance, the impedance drop, the impedance minimum and the first impedance rise. The system also includes an electrosurgical instrument including at least one active electrode adapted to apply electrosurgical energy to tissue for treatment.

13 Claims, 5 Drawing Sheets

U.S. PATENT DOCUMENTS

| | | |
|---|---|---|
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,167,658 A | 12/1992 | Ensslin |

| | | | | | | |
|---|---|---|---|---|---|---|
| 5,190,517 A | 3/1993 | Zieve et al. | | 5,584,830 A | 12/1996 | Ladd et al. |
| 5,196,008 A | 3/1993 | Kuenecke | | 5,588,432 A | 12/1996 | Crowley |
| 5,196,009 A | 3/1993 | Kirwan, Jr. | | 5,596,466 A | 1/1997 | Ochi |
| 5,201,900 A | 4/1993 | Nardella | | 5,599,344 A | 2/1997 | Paterson |
| 5,207,691 A | 5/1993 | Nardella | | 5,599,345 A | 2/1997 | Edwards et al. |
| 5,230,623 A | 7/1993 | Guthrie et al. | | 5,599,348 A | 2/1997 | Gentelia et al. |
| 5,233,515 A | 8/1993 | Cosman | | 5,605,150 A | 2/1997 | Radons et al. |
| 5,249,121 A | 9/1993 | Baum et al. | | 5,613,966 A | 3/1997 | Makower et al. |
| 5,254,117 A | 10/1993 | Rigby et al. | | 5,626,575 A | 5/1997 | Crenner |
| RE34,432 E | 11/1993 | Bertrand | | 5,628,745 A | 5/1997 | Bek |
| 5,267,994 A | 12/1993 | Gentelia et al. | | 5,643,330 A | 7/1997 | Holsheimer et al. |
| 5,267,997 A | 12/1993 | Farin | | 5,647,869 A | 7/1997 | Goble et al. |
| 5,281,213 A | 1/1994 | Milder et al. | | 5,647,871 A | 7/1997 | Levine et al. |
| 5,300,068 A | 4/1994 | Rosar et al. | | 5,651,780 A | 7/1997 | Jackson et al. |
| 5,300,070 A | 4/1994 | Gentelia | | 5,658,322 A | 8/1997 | Fleming |
| 5,318,563 A | 6/1994 | Malis et al. | | 5,660,567 A | 8/1997 | Nierlich et al. |
| 5,323,778 A | 6/1994 | Kandarpa et al. | | 5,674,217 A | 10/1997 | Wahlstrom et al. |
| 5,324,283 A | 6/1994 | Heckele | | 5,685,840 A | 11/1997 | Schechter et al. |
| 5,330,518 A | 7/1994 | Neilson et al. | | 5,688,267 A | 11/1997 | Panescu et al. |
| 5,334,183 A | 8/1994 | Wuchinich | | 5,693,042 A | 12/1997 | Boiarski et al. |
| 5,334,193 A | 8/1994 | Nardella | | 5,694,304 A | 12/1997 | Telefus et al. |
| 5,341,807 A | 8/1994 | Nardella | | 5,695,494 A | 12/1997 | Becker |
| 5,342,356 A | 8/1994 | Ellman | | 5,696,441 A | 12/1997 | Mak et al. |
| 5,342,357 A | 8/1994 | Nardella | | 5,702,386 A | 12/1997 | Stern et al. |
| 5,342,409 A | 8/1994 | Mullett | | 5,702,429 A | 12/1997 | King |
| 5,348,554 A | 9/1994 | Imran et al. | | 5,707,369 A | 1/1998 | Vaitekunas et al. |
| 5,370,645 A | 12/1994 | Klicek et al. | | 5,712,772 A | 1/1998 | Telefus et al. |
| 5,370,672 A | 12/1994 | Fowler et al. | | 5,713,896 A | 2/1998 | Nardella |
| 5,370,675 A | 12/1994 | Edwards et al. | | 5,718,246 A | 2/1998 | Vona |
| 5,372,596 A | 12/1994 | Klicek et al. | | 5,720,744 A | 2/1998 | Eggleston et al. |
| 5,383,874 A | 1/1995 | Jackson | | 5,722,975 A | 3/1998 | Edwards et al. |
| 5,383,876 A | 1/1995 | Nardella | | 5,729,448 A | 3/1998 | Haynie et al. |
| 5,383,917 A | 1/1995 | Desai et al. | | 5,733,281 A | 3/1998 | Nardella |
| 5,385,148 A | 1/1995 | Lesh et al. | | 5,749,869 A | 5/1998 | Lindenmeier et al. |
| 5,400,267 A | 3/1995 | Denen et al. | | 5,749,871 A | 5/1998 | Hood et al. |
| 5,403,311 A | 4/1995 | Abele et al. | | 5,755,715 A | 5/1998 | Stern |
| 5,403,312 A | 4/1995 | Yates et al. | | 5,766,165 A | 6/1998 | Gentelia et al. |
| 5,409,000 A | 4/1995 | Imran | | 5,769,847 A | 6/1998 | Panescu |
| 5,409,485 A | 4/1995 | Suda | | 5,772,659 A | 6/1998 | Becker et al. |
| 5,413,573 A | 5/1995 | Koivukangas | | 5,792,138 A | 8/1998 | Shipp |
| 5,414,238 A | 5/1995 | Steigerwald et al. | | 5,797,902 A | 8/1998 | Netherly |
| 5,417,719 A | 5/1995 | Hull et al. | | 5,797,941 A * | 8/1998 | Schulze et al. ................ 606/171 |
| 5,422,567 A | 6/1995 | Matsunaga | | 5,814,092 A | 9/1998 | King |
| 5,423,808 A | 6/1995 | Edwards et al. | | 5,817,093 A | 10/1998 | Williamson, IV et al. |
| 5,423,809 A | 6/1995 | Klicek | | 5,820,568 A | 10/1998 | Willis |
| 5,423,810 A | 6/1995 | Goble et al. | | 5,827,271 A | 10/1998 | Bussey et al. |
| 5,425,704 A | 6/1995 | Sakurai et al. | | 5,830,212 A | 11/1998 | Cartmell |
| 5,430,434 A | 7/1995 | Lederer et al. | | 5,836,909 A | 11/1998 | Cosmescu |
| 5,432,459 A | 7/1995 | Thompson | | 5,836,943 A | 11/1998 | Miller, III |
| 5,433,739 A | 7/1995 | Sluijter et al. | | 5,836,990 A | 11/1998 | Li |
| 5,436,566 A | 7/1995 | Thompson | | 5,846,236 A | 12/1998 | Lindenmeier et al. |
| 5,438,302 A | 8/1995 | Goble | | 5,868,737 A | 2/1999 | Taylor et al. |
| 5,443,463 A | 8/1995 | Stern et al. | | 5,868,739 A | 2/1999 | Lindenmeier et al. |
| 5,445,635 A | 8/1995 | Denen | | 5,868,740 A | 2/1999 | LeVeen et al. |
| 5,445,638 A * | 8/1995 | Rydell et al. .................... 606/51 | | 5,871,481 A | 2/1999 | Kannenberg et al. |
| 5,451,224 A | 9/1995 | Goble et al. | | 5,897,552 A | 4/1999 | Edwards et al. |
| 5,458,597 A | 10/1995 | Edwards et al. | | 5,908,444 A | 6/1999 | Azure |
| 5,462,521 A | 10/1995 | Brucker et al. | | 5,913,882 A | 6/1999 | King |
| 5,472,441 A | 12/1995 | Edwards et al. | | 5,921,982 A | 7/1999 | Lesh et al. |
| 5,472,443 A | 12/1995 | Cordis et al. | | 5,925,070 A | 7/1999 | King et al. |
| 5,480,399 A | 1/1996 | Hebborn | | 5,931,836 A | 8/1999 | Hatta et al. |
| 5,483,952 A | 1/1996 | Aranyi | | 5,938,690 A | 8/1999 | Law et al. |
| 5,496,312 A | 3/1996 | Klicek | | 5,948,007 A | 9/1999 | Starkenbaum et al. |
| 5,496,313 A | 3/1996 | Gentelia et al. | | 5,951,545 A | 9/1999 | Schilling |
| 5,500,012 A | 3/1996 | Brucker et al. | | 5,951,546 A | 9/1999 | Lorentzen |
| 5,500,616 A | 3/1996 | Ochi | | 5,954,686 A | 9/1999 | Garito et al. |
| 5,514,129 A | 5/1996 | Smith | | 5,954,717 A | 9/1999 | Behl et al. |
| 5,520,684 A | 5/1996 | Imran | | 5,954,719 A | 9/1999 | Chen et al. |
| 5,531,774 A | 7/1996 | Schulman et al. | | 5,961,344 A | 10/1999 | Rosales et al. |
| 5,534,018 A | 7/1996 | Wahlstrand et al. | | 5,971,980 A | 10/1999 | Sherman |
| 5,536,267 A | 7/1996 | Edwards et al. | | 5,976,128 A | 11/1999 | Schilling et al. |
| 5,540,681 A | 7/1996 | Strul et al. | | 5,983,141 A | 11/1999 | Sluijter et al. |
| 5,540,683 A | 7/1996 | Ichikawa | | 6,010,499 A | 1/2000 | Cobb |
| 5,540,684 A | 7/1996 | Hassler, Jr. | | 6,014,581 A | 1/2000 | Whayne et al. |
| 5,556,396 A | 9/1996 | Cohen et al. | | 6,033,399 A | 3/2000 | Gines |
| 5,558,671 A | 9/1996 | Yates | | 6,044,283 A | 3/2000 | Fein et al. |
| 5,569,242 A | 10/1996 | Lax et al. | | 6,053,910 A | 4/2000 | Fleenor |
| 5,571,147 A | 11/1996 | Sluijter et al. | | 6,053,912 A | 4/2000 | Panescu et al. |
| 5,573,533 A | 11/1996 | Strul | | 6,055,458 A | 4/2000 | Cochran et al. |

| | | | | | | |
|---|---|---|---|---|---|---|
| 6,056,745 | A | 5/2000 | Panescu et al. | 6,645,198 | B1 | 11/2003 | Bommannan et al. |
| 6,056,746 | A | 5/2000 | Goble et al. | 6,648,883 | B1 | 11/2003 | Francischelli |
| 6,063,075 | A | 5/2000 | Mihori | 6,652,514 | B2 | 11/2003 | Ellman |
| 6,063,078 | A | 5/2000 | Wittkampf | 6,663,623 | B1 | 12/2003 | Oyama et al. |
| 6,068,627 | A | 5/2000 | Orszulak et al. | 6,663,624 | B2 | 12/2003 | Edwards |
| 6,074,386 | A | 6/2000 | Goble et al. | 6,666,860 | B1 | 12/2003 | Takahashi |
| 6,074,388 | A | 6/2000 | Tockweiler et al. | 6,679,875 | B2 | 1/2004 | Honda |
| 6,080,149 | A | 6/2000 | Huang et al. | 6,682,527 | B2 | 1/2004 | Strul |
| 6,093,186 | A | 7/2000 | Goble | 6,685,700 | B2 | 2/2004 | Behl |
| 6,102,497 | A | 8/2000 | Ehr et al. | 6,685,701 | B2 | 2/2004 | Orszulak et al. |
| 6,113,591 | A | 9/2000 | Whayne et al. | 6,685,703 | B2 | 2/2004 | Pearson et al. |
| 6,113,596 | A | 9/2000 | Hooven | 6,689,131 | B2 | 2/2004 | McClurken |
| 6,123,702 | A | 9/2000 | Swanson et al. | 6,692,489 | B1 | 2/2004 | Heim |
| 6,132,429 | A | 10/2000 | Baker | 6,693,782 | B1 | 2/2004 | Lash |
| 6,142,992 | A | 11/2000 | Cheng et al. | 6,712,813 | B2 | 3/2004 | Ellman |
| 6,155,975 | A | 12/2000 | Urich et al. | 6,730,080 | B2 | 5/2004 | Harano |
| 6,162,217 | A | 12/2000 | Kannenberg et al. | 6,733,495 | B1 | 5/2004 | Bek |
| 6,171,304 | B1 | 1/2001 | Netherly et al. | 6,733,498 | B2 | 5/2004 | Paton |
| 6,188,211 | B1 | 2/2001 | Rincon-Mora et al. | 6,740,079 | B1 | 5/2004 | Eggers |
| 6,203,541 | B1 | 3/2001 | Keppel | 6,740,085 | B2 | 5/2004 | Hareyama |
| 6,210,403 | B1 | 4/2001 | Klicek | 6,755,825 | B2 | 6/2004 | Shoenman et al. |
| 6,222,356 | B1 | 4/2001 | Taghizadeh-Kaschani | 6,758,846 | B2 | 7/2004 | Goble et al. |
| 6,228,080 | B1 | 5/2001 | Gines | 6,783,523 | B2 | 8/2004 | Qin |
| 6,228,081 | B1 | 5/2001 | Goble | 6,786,905 | B2 | 9/2004 | Swanson et al. |
| 6,231,569 | B1 | 5/2001 | Bek | 6,790,206 | B2 | 9/2004 | Panescu |
| 6,235,020 | B1 | 5/2001 | Cheng et al. | 6,796,981 | B2 | 9/2004 | Wham |
| 6,238,387 | B1 | 5/2001 | Miller, III | 6,824,539 | B2 | 11/2004 | Novak |
| 6,238,388 | B1 | 5/2001 | Ellman | 6,830,569 | B2 | 12/2004 | Thompson |
| 6,241,725 | B1 | 6/2001 | Cosman | 6,843,789 | B2 | 1/2005 | Goble |
| 6,245,065 | B1 | 6/2001 | Panescu | 6,849,073 | B2 | 2/2005 | Hoey |
| 6,246,912 | B1 | 6/2001 | Sluijter et al. | 6,855,141 | B2 | 2/2005 | Lovewell |
| 6,251,106 | B1 | 6/2001 | Becker et al. | 6,855,142 | B2 | 2/2005 | Harano |
| 6,258,085 | B1 | 7/2001 | Eggleston | 6,860,881 | B2 | 3/2005 | Sturm |
| 6,261,285 | B1 | 7/2001 | Novak | 6,864,686 | B2 | 3/2005 | Novak |
| 6,261,286 | B1 | 7/2001 | Goble et al. | 6,875,210 | B2 | 4/2005 | Refior |
| 6,273,886 | B1 | 8/2001 | Edwards | 6,893,435 | B2 | 5/2005 | Goble |
| 6,275,786 | B1 | 8/2001 | Daners | 6,923,804 | B2 | 8/2005 | Eggers et al. |
| 6,293,941 | B1 | 9/2001 | Strul | 6,929,641 | B2 | 8/2005 | Goble et al. |
| 6,293,942 | B1 | 9/2001 | Goble et al. | 6,939,346 | B2 | 9/2005 | Kannenberg et al. |
| 6,296,636 | B1 | 10/2001 | Cheng et al. | 6,939,347 | B2 | 9/2005 | Thompson |
| 6,306,131 | B1 | 10/2001 | Hareyama et al. | 6,942,660 | B2 | 9/2005 | Pantera et al. |
| 6,306,134 | B1 | 10/2001 | Goble et al. | 6,948,503 | B2 | 9/2005 | Refior et al. |
| 6,309,386 | B1 | 10/2001 | Bek | 6,953,461 | B2 * | 10/2005 | McClurken et al. ............ 606/51 |
| 6,325,799 | B1 | 12/2001 | Goble | 6,966,907 | B2 | 11/2005 | Goble |
| 6,337,998 | B1 | 1/2002 | Behl et al. | 6,989,010 | B2 | 1/2006 | Francischelli et al. |
| 6,338,657 | B1 | 1/2002 | Harper et al. | 6,994,704 | B2 | 2/2006 | Qin et al. |
| 6,350,262 | B1 | 2/2002 | Ashley | 6,994,707 | B2 | 2/2006 | Ellman et al. |
| 6,358,245 | B1 | 3/2002 | Edwards | 7,001,381 | B2 | 2/2006 | Harano et al. |
| 6,364,877 | B1 | 4/2002 | Goble et al. | 7,004,174 | B2 | 2/2006 | Eggers et al. |
| 6,383,183 | B1 | 5/2002 | Sekino et al. | 7,041,096 | B2 | 5/2006 | Malis et al. |
| 6,391,024 | B1 | 5/2002 | Sun et al. | 7,044,948 | B2 | 5/2006 | Keppel |
| 6,398,779 | B1 | 6/2002 | Buysse et al. | 7,044,949 | B2 | 5/2006 | Orszulak et al. |
| 6,398,781 | B1 | 6/2002 | Goble et al. | 7,060,063 | B2 | 6/2006 | Marion et al. |
| 6,402,741 | B1 | 6/2002 | Keppel et al. | 7,062,331 | B2 | 6/2006 | Zarinetchi et al. |
| 6,402,743 | B1 | 6/2002 | Orszulak et al. | 7,063,692 | B2 | 6/2006 | Sakurai et al. |
| 6,416,509 | B1 | 7/2002 | Goble et al. | 7,066,933 | B2 | 6/2006 | Hagg |
| 6,436,096 | B1 | 8/2002 | Hareyama | 7,122,031 | B2 | 10/2006 | Edwards et al. |
| 6,451,015 | B1 | 9/2002 | Rittman, III et al. | 7,131,860 | B2 | 11/2006 | Sartor et al. |
| 6,458,121 | B1 | 10/2002 | Rosenstock | 7,137,980 | B2 * | 11/2006 | Buysse et al. .................. 606/34 |
| 6,464,689 | B1 | 10/2002 | Qin | 7,147,638 | B2 | 12/2006 | Chapman et al. |
| 6,464,696 | B1 | 10/2002 | Oyama | 7,160,293 | B2 | 1/2007 | Sturm et al. |
| 6,498,466 | B1 | 12/2002 | Edwards | 7,172,591 | B2 | 2/2007 | Harano et al. |
| 6,506,189 | B1 | 1/2003 | Rittman, III et al. | 7,175,618 | B2 | 2/2007 | Dabney et al. |
| 6,508,815 | B1 | 1/2003 | Strul | 7,175,621 | B2 | 2/2007 | Heim et al. |
| 6,511,476 | B2 | 1/2003 | Hareyama | 7,211,081 | B2 | 5/2007 | Goble |
| 6,511,478 | B1 | 1/2003 | Burnside et al. | 7,214,224 | B2 | 5/2007 | Goble |
| 6,517,538 | B1 | 2/2003 | Jacob et al. | 7,220,260 | B2 | 5/2007 | Fleming et al. |
| 6,524,308 | B1 | 2/2003 | Muller et al. | 7,247,155 | B2 * | 7/2007 | Hoey et al. ...................... 606/34 |
| 6,547,786 | B1 | 4/2003 | Goble | 7,250,746 | B2 | 7/2007 | Oswald et al. |
| 6,558,376 | B2 | 5/2003 | Bishop | 7,255,694 | B2 | 8/2007 | Keppel |
| 6,560,470 | B1 | 5/2003 | Pologe | 7,282,048 | B2 | 10/2007 | Goble et al. |
| 6,562,037 | B2 | 5/2003 | Paton | 7,300,435 | B2 | 11/2007 | Wham et al. |
| 6,565,559 | B2 | 5/2003 | Eggleston | 7,303,557 | B2 | 12/2007 | Wham et al. |
| 6,575,969 | B1 | 6/2003 | Rittman, III et al. | 7,364,577 | B2 | 4/2008 | Wham et al. |
| 6,582,427 | B1 | 6/2003 | Goble et al. | 7,367,972 | B2 | 5/2008 | Francischelli et al. |
| 6,620,157 | B1 | 9/2003 | Dabney et al. | RE40,388 | E | 6/2008 | Gines |
| 6,623,423 | B2 | 9/2003 | Sakurai | 7,396,336 | B2 | 7/2008 | Orszulak et al. |
| 6,629,973 | B1 | 10/2003 | Wardell et al. | 2001/0014804 | A1 | 8/2001 | Goble et al. |
| 6,635,057 | B2 | 10/2003 | Harano | 2001/0029315 | A1 | 10/2001 | Sakurai et al. |

| | | |
|---|---|---|
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0158551 A1 | 8/2003 | Paton et al. |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0070896 A1 | 3/2005 | Daniel et al. |
| 2005/0101948 A1 | 5/2005 | Harano et al. |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2010/0042093 A9 * | 2/2010 | Wham et al. .................. 606/34 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0640317 A1 | 3/1995 |
| EP | 0 694 291 | 1/1996 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1 472 984 A1 | 11/2004 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1645235 | 4/2006 |
| EP | 0880220 B1 | 6/2006 |
| EP | 1707143 | 10/2006 |
| EP | 1 810 628 A1 | 7/2007 |
| EP | 1 810 633 A2 | 7/2007 |
| EP | 1810628 | 7/2007 |
| EP | 1810630 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |

| | | |
|---|---|---|
| GB | 855459 | 11/1960 |
| GB | 902775 | 8/1962 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO 94/10922 A1 | 5/1994 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO 96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060849 | 7/2005 |

OTHER PUBLICATIONS

International Search Report EP 07010673.7; dated Sep. 24, 2007.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2;(Mar. 2005); 160-164.
International Search Report EP 07015602.1; dated Dec. 3, 2007.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson at al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman at al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg at al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps 8 Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
European Search Report for EP 10 18 0965 dated Jan. 26, 2011.
Extended European Search Report from European Patent Application No. 07001494.9 mailed Mar. 7, 2011.
European Search Report for EP 10 18 0964 dated Dec. 22, 2010.

* cited by examiner

SYSTEM AND METHOD FOR MEASURING INITIAL TISSUE IMPEDANCE

BACKGROUND

1. Technical Field

The present disclosure relates to a system and method for performing electrosurgical procedures. More particularly, the present disclosure relates to a system and method for measuring tissue properties during tissue sealing procedures.

2. Background of Related Art

Electrosurgery involves application of high radio frequency electrical current to a surgical site to cut, ablate, coagulate, cauterize, desiccate or seal tissue. Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, are used for less invasive endoscopic surgical procedures. Electrosurgical forceps (open or endoscopic) utilize mechanical clamping action and electrical energy to effect hemostasis on the clamped tissue. The forceps includes electrosurgical sealing plates which apply the electrosurgical energy to the clamped tissue. By controlling the intensity, frequency and duration of the electrosurgical energy applied through the sealing plates to the tissue, the surgeon can coagulate, cauterize and/or seal tissue. Selecting the appropriate energy parameters during the sealing procedure allows for efficient application of energy to tissue. Thus, a need exists to develop an electrosurgical system which effectively and consistently seals tissue.

SUMMARY

The present disclosure relates to a system and method for performing electrosurgical procedures. The system includes an electrosurgical generator and an instrument (e.g., electrosurgical forceps). The generator supplies an initial interrogatory signal at constant voltage to tissue and measures initial tissue impedance response. Thereafter, the generator analyzes the initial tissue impedance response and selects corresponding treatment parameters that are used to select corresponding output of the generator.

According to one aspect of the present disclosure an electrosurgical system is disclosed. The system includes an electrosurgical generator adapted to supply electrosurgical energy to tissue. The generator is further adapted to supply an electrical signal having at least one substantially constant value to tissue to determine initial tissue impedance response. The generator includes sensor circuitry adapted to continuously monitor tissue impedance response, wherein the tissue impedance response includes an initial impedance, an impedance drop, an impedance minimum and a first impedance rise. The generator also includes a microprocessor adapted to generate at least one tissue treatment parameter as a function of one of the initial impedance, the impedance drop, the impedance minimum and the first impedance rise. The system also includes an electrosurgical instrument including at least one active electrode adapted to apply electrosurgical energy to tissue for treatment.

According to another aspect of the present disclosure, a method for performing electrosurgical procedures is disclosed. The method includes the steps of supplying an electrical signal having at least one substantially constant value to tissue to determine initial tissue impedance response, wherein the initial tissue impedance response includes at least one of an initial impedance, an impedance drop, an impedance minimum and a first impedance rise. The method also includes the step of continuously monitoring initial tissue impedance response. The method further includes the step of generating at least one tissue treatment parameter as a function of one of the initial impedance, the impedance drop, the impedance minimum and the first impedance rise.

According to a further aspect of the present disclosure, an electrosurgical generator is disclosed. The electrosurgical generator includes an RF output stage adapted to supply electrosurgical energy to tissue and to supply an electrical signal having at least one substantially constant value to tissue to determine initial tissue impedance response. The generator also includes sensor circuitry adapted to continuously monitor initial tissue impedance response, wherein the initial tissue impedance response includes at least one of an initial impedance, an impedance drop, an impedance minimum and a first impedance rise. The generator further includes a microprocessor adapted to generate at least one tissue treatment parameter as a function of the initial impedance, the impedance drop, the impedance minimum and the first impedance rise.

BRIEF DESCRIPTION OF THE DRAWINGS

Various embodiments of the present disclosure are described herein with reference to the drawings wherein.

DETAILED DESCRIPTION

Figure 1:
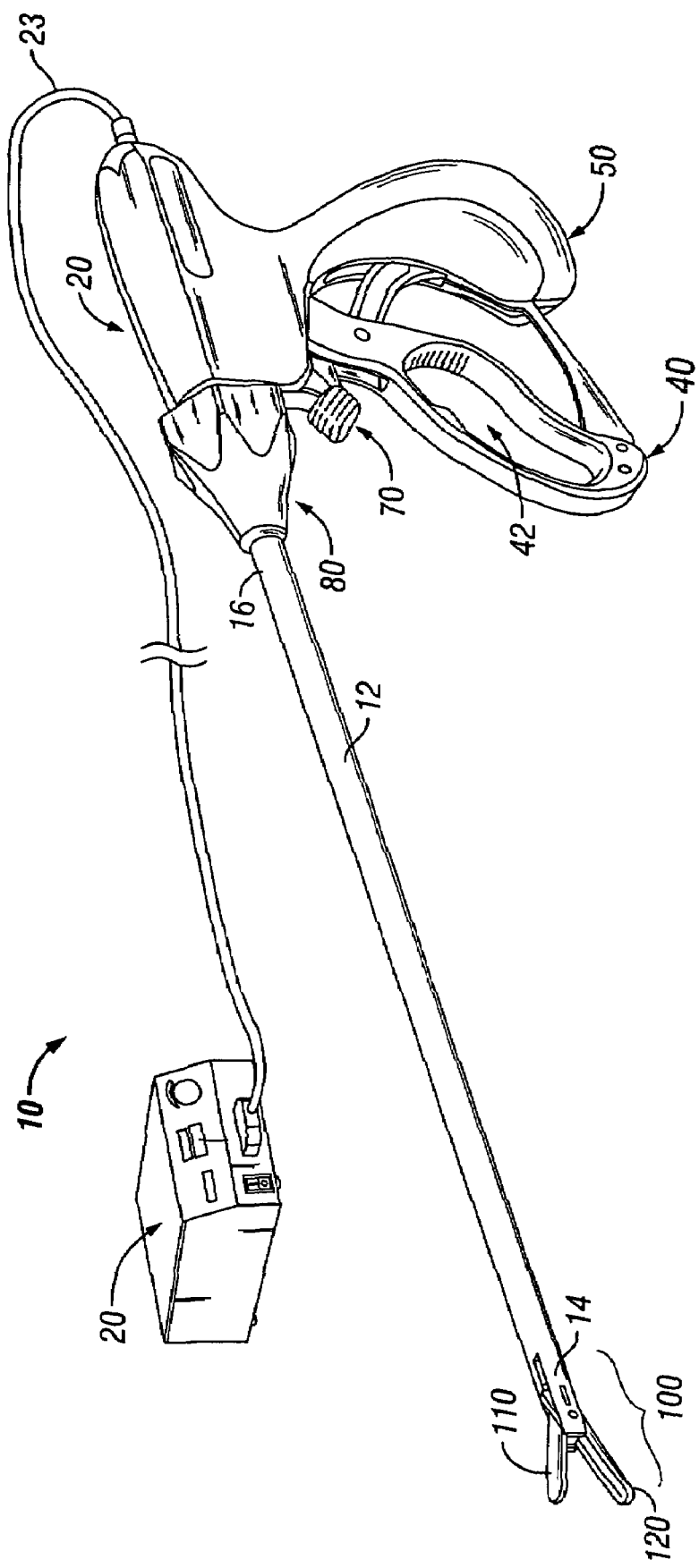
FIG. 1 is a perspective view of an electrosurgical system according to the present disclosure.

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems FIG. 1 shows an endoscopic bipolar electrosurgical system according to the present disclosure which includes an electrosurgical forceps 10. Those skilled in the art will understand that the invention according to the present disclosure may be adapted for use with either an endoscopic instrument as shown in FIG. 1 or an open instrument. More particularly, forceps 10 generally includes a housing 21, a handle assembly 40, a rotating assembly 80, and a trigger assembly 70 which mutually cooperate with the end effector assembly 100 to grasp and treat tissue. The forceps 10 also includes a shaft 12 which has a distal end 14 that mechanically engages the end effector assembly 100 and a proximal end 16 which mechanically engages the housing 21 proximate the rotating assembly 80. Handle assembly 40 includes a fixed handle 50 and a movable handle 42. Handle 42 moves relative to the fixed handle 50 to actuate the end effector assembly 100 and enable a user to grasp and manipulate tissue. Electrosurgical RF energy is supplied to the forceps 10 by generator 20 via a supply line connected to the active electrode and returned through a return line connected to the return electrode. The supply and return lines are enclosed within a cable 23.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust the RF energy, waveform, and other parameters to achieve the desired waveform suitable for a particular task (e.g., coagulating, tissue sealing, intensity setting, etc.). It is also envisioned that the forceps 10 may include a plurality of input controls which may be redundant with certain input controls of the generator 20. Placing the input controls at the forceps 10 allows for easier and faster modification of RF energy parameters during the surgical procedure without requiring interaction with the generator 20.

The end effector assembly 100 includes opposing jaw members 110 and 120 having electrically conductive sealing plate 112 and 122, respectively, attached thereto for conducting electrosurgical energy through tissue. More particularly, the jaw members 110 and 120 move in response to movement of the handle 42 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto. Further details relating to one envisioned endoscopic forceps is disclosed in commonly-owned U.S. application Ser. No. 10/474,169 entitled "VESSEL SEALER AND DIVIDER" the entire contents of which is incorporated by reference herein.

The jaw members 110 and 120 are activated using a drive assembly (not shown) enclosed within the housing 21. The drive assembly cooperates with the movable handle 42 to impart movement of the jaw members 110 and 120 from the open position to the clamping or closed position. Examples of a handle assemblies are shown and described in the above identified application as well as commonly-owned U.S. application Ser. No. 10/369,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

Jaw members 110 and 120 also include insulators 116 and 126 which together with the outer, non-conductive plates of the jaw members 110 and 120 are configured to limit and/or reduce many of the known undesirable effects related to tissue sealing, e.g., flashover, thermal spread and stray current dissipation.

The handle assembly 40 of this particular disclosure may include a four-bar mechanical linkage which provides a unique mechanical advantage when sealing tissue between the jaw members 110 and 120. For example, once the desired position for the sealing site is determined and the jaw members 110 and 120 are properly positioned, handle 42 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

Figure 2:
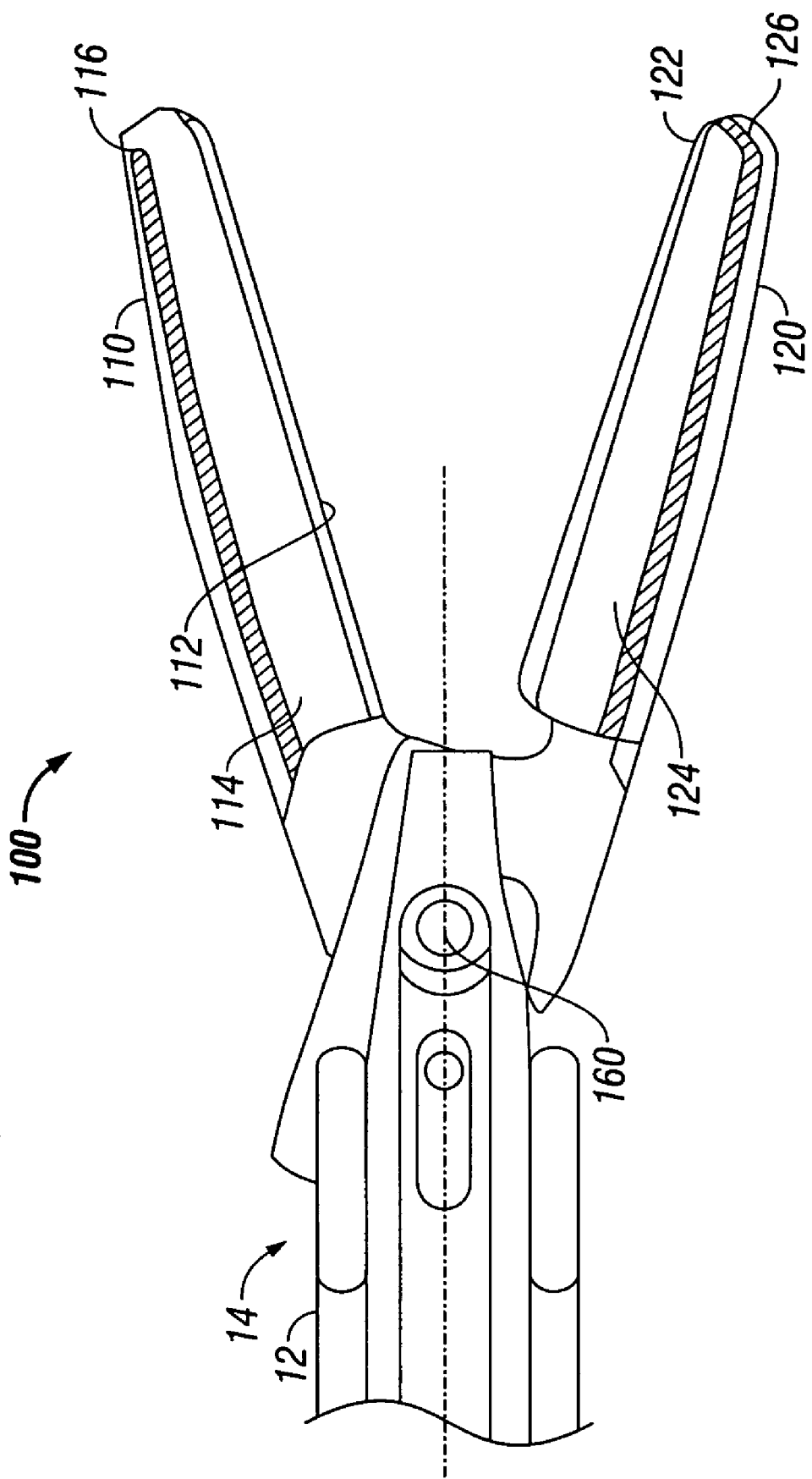
FIG. 2 is a side, partial internal view of an endoscopic forceps according to the present disclosure.

As shown in FIGS. 1-2, the forceps 10 also includes a trigger 70 which advances a knife (not explicitly shown) disposed within the end effector assembly 100. Once a tissue seal is formed, the user activates the trigger 70 to separate the tissue along the tissue seal. Knife preferably includes a sharpened edge for severing the tissue held between the jaw members 110 and 120 at the tissue sealing site. A longitudinally-oriented channel (not explicitly shown) is defined in an electrically conductive sealing plate 112 extending from the proximal end to the distal end thereof. The channel facilitates longitudinal reciprocation of the knife along a preferred cutting plane to effectively and accurately separate the tissue along a formed tissue seal.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1 and 2, the end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 40. In either of these two instances, the forceps 10 may be either partially disposable or reposable, such as where a new or different end effector assembly 100 or end effector assembly 100 and shaft 12 are used to selectively replace the old end effector assembly 100 as needed.

Figure 3:
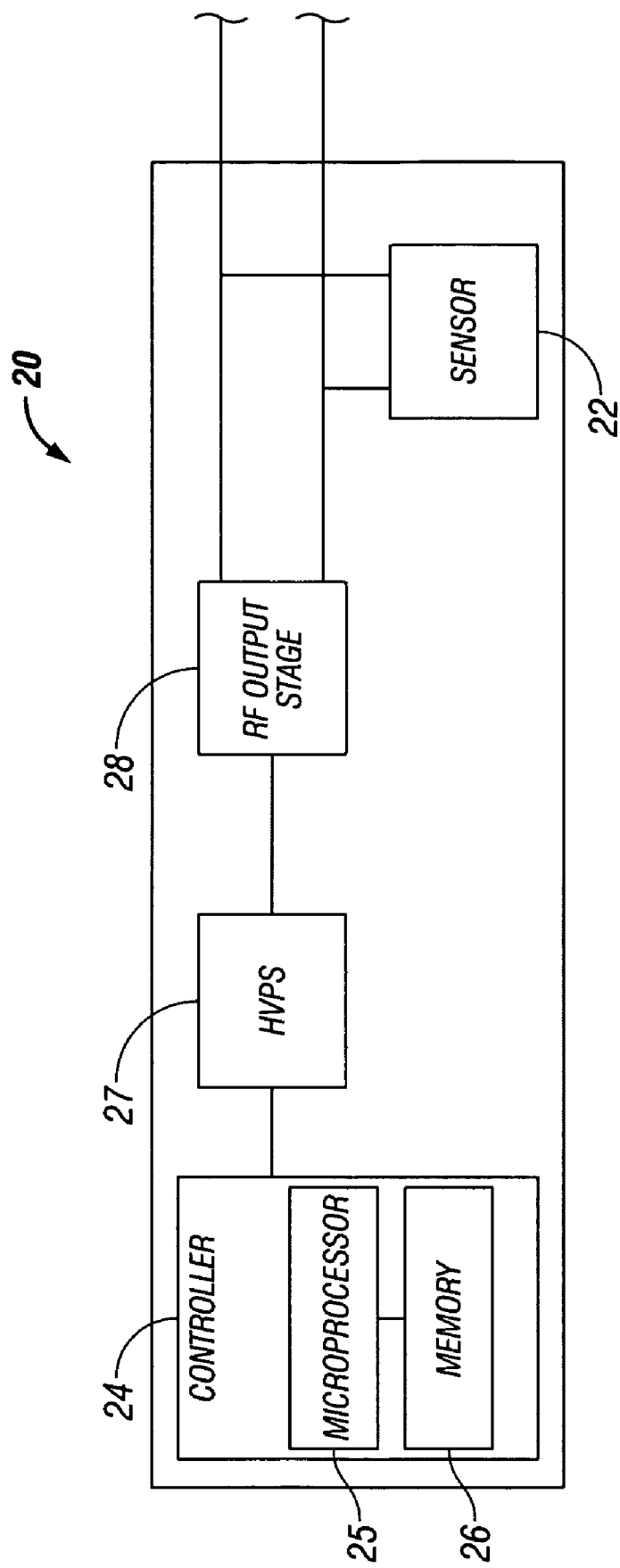
FIG. 3 is a schematic block diagram of a generator system according to the present disclosure.

FIG. 3 shows a schematic block diagram of the generator 20 having a controller 24, a high voltage DC power supply 27 ("HVPS") and an RF output stage 28. The HVPS 27 provides high voltage DC power to an RF output stage 28 which then converts high voltage DC power into RF energy and delivers the RF energy to the active electrode 24. In particular, the RF output stage 28 generates sinusoidal waveforms of high frequency RF energy. The RF output stage 28 is configured to generate a plurality of waveforms having various duty cycles, peak voltages, crest factors, and other parameters. Certain types of waveforms are suitable for specific electrosurgical modes. For instance, the RF output stage 28 generates a 100% duty cycle sinusoidal waveform in cut mode, which is best suited for dissecting tissue and a 25% duty cycle waveform in coagulation mode, which is best used for cauterizing tissue to stop bleeding.

The controller 24 includes a microprocessor 25 operably connected to a memory 26 which may be volatile type memory (e.g., RAM) and/or non-volatile type memory (e.g., flash media, disk media, etc.). The microprocessor 25 includes an output port which is operably connected to the HVPS 27 and/or RF output stage 28 allowing the microprocessor 25 to control the output of the generator 20 according to either open and/or closed control loop schemes.

A closed loop control scheme is a feedback control loop wherein sensor circuitry 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28 which then adjust DC and/or RF power supply, respectively. The controller 24 also receives input signals from the input controls of the generator 20 or the forceps 10. The controller 24 utilizes the input signals to adjust power outputted by the generator 20 and/or performs other control functions thereon.

Figure 4:
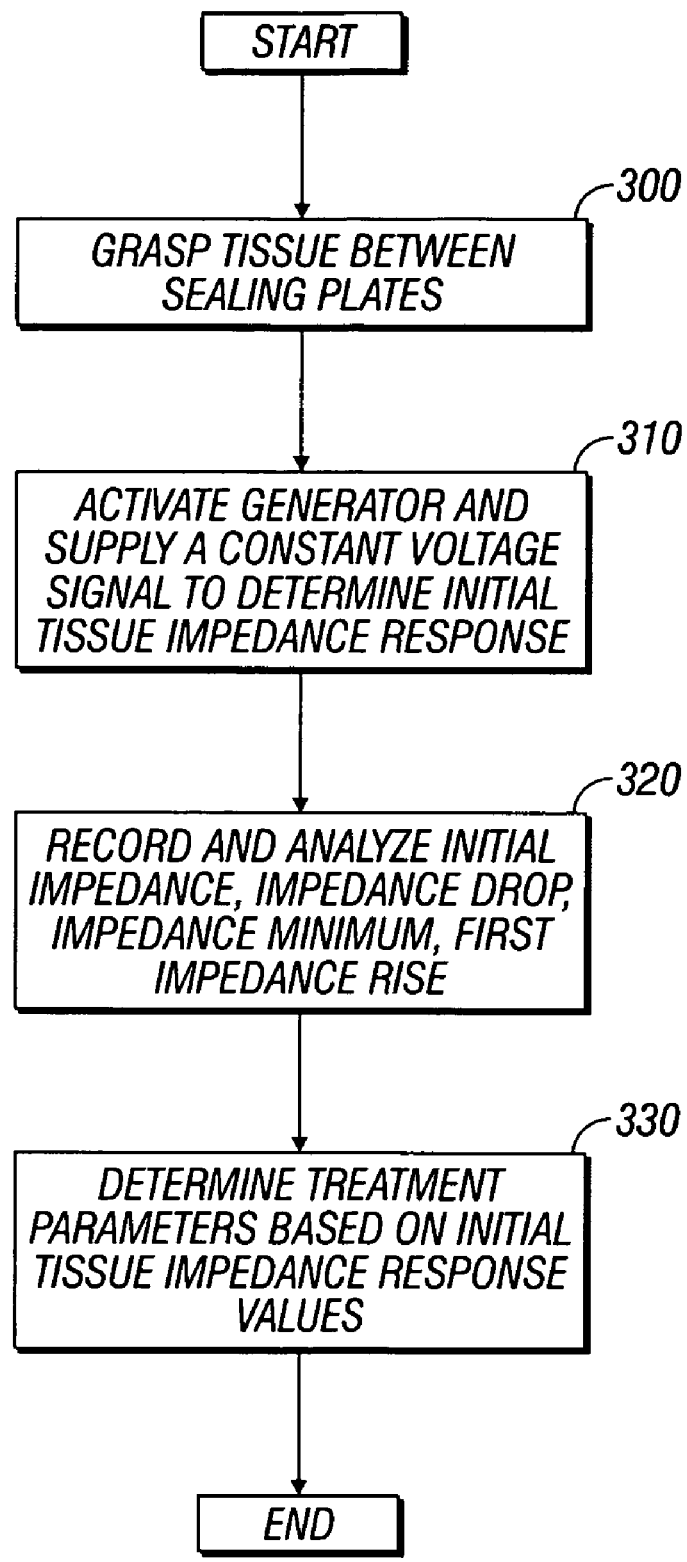
FIG. 4 is a flow diagram illustrating a method according to the present disclosure.

FIG. 4 shows a method according to the present disclosure for controlling output of the generator in response to monitored tissue impedance. In step 300, the forceps 10 is positioned to grasp tissue using jaw members 110 and 120. In step 310, the sealing plates 112 and 122 are activated and are in contact with the tissue but may not be fully closed. A constant voltage signal is applied for a predetermined period of time (e.g., first 2 to 3 seconds) to determine initial tissue impedance response. This occurs prior to treatment of tissue via electrosurgical energy. Other electrical signals having one or more substantially constant values, such as constant power, current, and energy, may also be applied to tissue to determine initial tissue impedance response.

The initial tissue impedance response describes the natural tissue state and is used in subsequent calculations to determine a variety of seal parameters (e.g., duration of energy application, amount of energy to be applied, etc.). The impedance is monitored by the sensor circuitry 22. In particular, voltage and current signals are monitored and corresponding impedance values are calculated with the sensor circuitry 22 and/or with the microprocessor 25. Power and other energy properties may also be calculated based on collected voltage and current signals. The microprocessor 25 stores the collected voltage, current, and impedance within the memory 26.

Figure 5A:
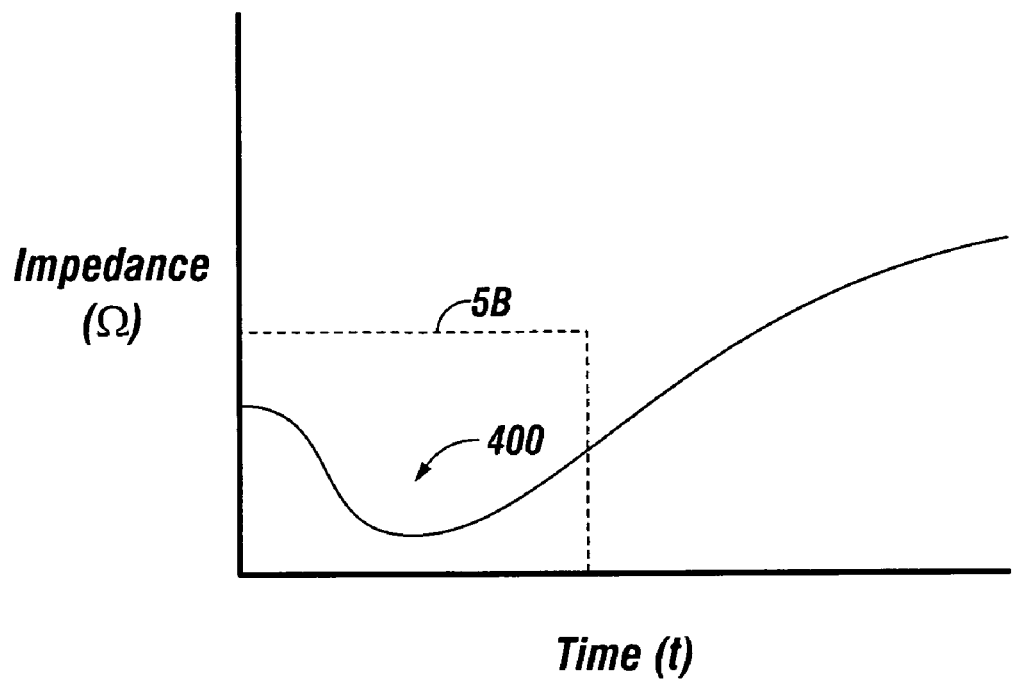
FIGS. 5A-B are illustrative graphs showing impedance values over time.
Figure 5B:
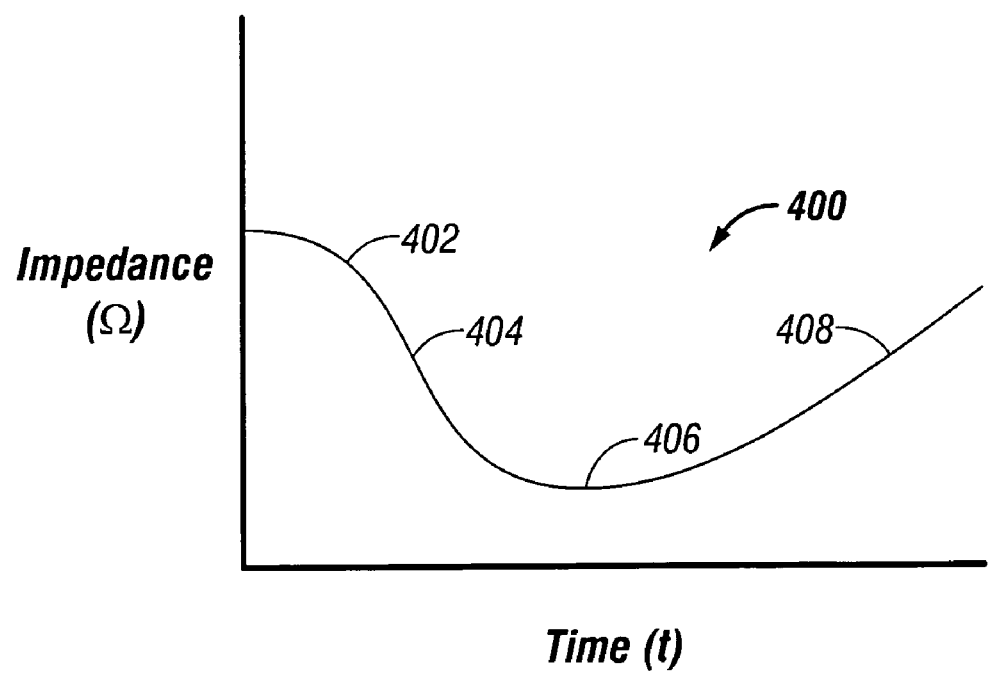

Exemplary impedance response is illustrated in FIGS. 5A-B which show a graph of impedance versus time. In particular, FIG. 5A shows changes in impedance during an entire tissue sealing procedure. As shown, the initial tissue impedance drops reaching a minimum impedance then rises at a first rate and then continues rising at a second rate which is generally slower than the first rate. FIG. 5B shows in more detail initial tissue impedance response that is represented by an impedance dip 400 that includes an initial impedance 402 followed by an impedance drop 404 that reaches an impedance minimum 406 and subsequently transitions into a first impedance rise 408.

In step 320, the initial tissue impedance response values, i.e., initial impedance 402, the impedance drop 404 (e.g., rate of drop), the impedance minimum 406 and the first impedance rise 40 (e.g., rate of rise) are recorded and analyzed. Impedance measurements as low as 50 Ohms or below are detected. The recorded initial tissue impedance response values provide detailed information concerning tissue between the jaws. For instance, the impedance drop 404 may be used to calculate the relationship between the gap distance between the electrodes and the amount of energy being supplied to tissue. Further, the impedance drop 404 may also be used to determine the type of tissue being grasped and the hydration levels thereof.

In step 330, the initial tissue impedance response values are used to determine treatment parameters (e.g., pressure to be applied to tissue, duration of energy application, amount of energy to be supplied, target impedance trajectory, etc.) for subsequent treatment of the tissue. This may be accomplished by populating a look up table that may be stored in the memory 26 with the impedance values. Based on these values corresponding tissue treatment parameters are loaded. The microprocessor 25 utilizes the loaded tissue treatment parameters to adjust output of the generator 20 as well as rate of closure and pressure exerted by the jaw members 110 and 120 on the tissue.

Those skilled in the art will appreciate that the measurement of initial impedance values and analysis thereof may be performed on a real-time basis providing for a system which is adaptive to various types of tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system comprising:
an electrosurgical generator adapted to supply electrosurgical energy to tissue, the generator further adapted to supply an electrical signal having at least one substantially constant value to tissue to determine initial tissue impedance response, the initial tissue impedance being used to determine an amount of the electrosurgical energy to tissue prior to tissue treatment, the generator including:
sensor circuitry adapted to continuously monitor initial tissue impedance response, wherein the initial tissue impedance response includes at least one of an initial impedance, an impedance drop, an impedance minimum and a first impedance rise; and
a microprocessor adapted to generate at least one tissue treatment parameter as a function of the initial tissue impedance response, including the at least one of initial impedance, the impedance drop, the impedance minimum and the first impedance rise, the microprocessor being in electrical communication with a memory to continuously store collected impedance and tissue information, the memory including at least a look up table for storing collected impedance values from a plurality of uses of the electrosurgical system; and an electrosurgical instrument including at least one active electrode adapted to apply electrosurgical energy to tissue for treatment, wherein the electrosurgical instrument is an electrosurgical forceps for sealing tissue, the forceps comprising:

at least one shaft member having an end effector assembly disposed at a distal end thereof; the end effector assembly including jaw members movable from a first position in spaced relation relative to one another to at least one subsequent position wherein the jaw members cooperate to grasp tissue therebetween; and a sealing plate attached to each of the jaw members in opposing relation thereto, said sealing plates adapted to connect to the electrosurgical generator such that said sealing plates communicate electrosurgical energy through tissue held therebetween;

wherein a tissue impedance profile during an entire tissue sealing procedure varies in a non-linear manner, such that in a first phase the initial tissue impedance drops to reach a minimum impedance, in a second phase rises at a first rate, and in a third phase rises at a second rate, the second rate being less than the first rate and the second rate stabilizing over a period of time.

2. An electro surgical system as in claim 1, wherein the microprocessor is further adapted to adjust output of the electrosurgical generator based on the at least one tissue parameter.

3. An electrosurgical system as in claim 1, wherein the at least one tissue parameter is selected from the group consisting of pressure to be applied to tissue, duration of energy application, amount of energy to be supplied and target impedance trajectory.

4. An electrosurgical system as in claim 1, wherein the constant value of the electrical signal is selected from the group consisting of constant voltage, constant current, constant power and constant energy.

5. A method for performing electrosurgical procedures comprising:

supplying an electrosurgical generator for providing an electrical signal having at least one substantially constant value to tissue to determine an initial tissue impedance response, the initial tissue impedance being used to determine an amount of electrosurgical energy to tissue prior to tissue treatment, said initial tissue response including at least one of an initial impedance, an impedance drop, an impedance minimum and a first impedance rise;

continuously monitoring said initial tissue impedance response;

generating, via a microprocessor, at least one tissue treatment parameter as a function of the initial tissue impedance response, including the at least one of initial impedance, the impedance drop, the impedance minimum and the first impedance rise, the microprocessor being in electrical communication with a memory to continuously store collected impedance and tissue information, the memory including at least a look up table for storing collected impedance values from the electrosurgical procedures performed; and providing an electrosurgical instrument including at least one active electrode for applying the electrosurgical energy to tissue, wherein the step of providing an electrosurgical instrument further includes providing an electrosurgical forceps for sealing tissue, the forceps comprising:

at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and a sealing plate attached to each of the jaw members in opposing relation thereto, said sealing plates adapted to connect to the electrosurgical generator such that said sealing plates communicate electrosurgical energy through tissue held therebetween;

wherein a tissue impedance profile during an entire tissue sealing procedure varies in a nonlinear manner, such that in a first phase the initial tissue impedance drops to reach a minimum impedance, in a second phase rises at a first rate, and in a third phase rises at a second rate, the second rate being less than the first rate and the second rate stabilizing over a period of time.

6. A method as in claim 5, further comprising the step of:
adjusting the output of the electrosurgical generator based on the at least one tissue parameter.

7. A method as in claim 6, wherein the at least one tissue parameter is selected from the group consisting of pressure to be applied to tissue, duration of energy application, amount of energy to be supplied and target impedance trajectory.

8. A method as in claim 5, wherein the constant value of the electrical signal is selected from the group consisting of constant voltage, constant current, constant power and constant energy.

9. An electrosurgical system adapted to supply electrosurgical energy to tissue comprising an electrosurgical generator having:

an RF output stage adapted to supply electrosurgical energy to tissue and further adapted to supply an electrical signal having at least one substantially constant value to tissue to determine an initial tissue impedance response, the initial tissue impedance being used to determine an amount of the electrosurgical energy to tissue prior to tissue treatment;

a sensor circuitry adapted to continuously monitor the initial tissue impedance response, wherein the initial tissue impedance response includes at least one of an initial impedance, an impedance drop, an impedance minimum and a first impedance rise; and a microprocessor adapted to generate at least one tissue treatment parameter as a function of the initial tissue impedance response, including the at least one of initial impedance, the impedance drop, the impedance minimum and the first impedance rise, the microprocessor being in electrical communication with a memory to continuously store collected impedance and tissue information, the memory including at least a look up table for storing collected impedance values from a plurality of uses of an electrosurgical instrument;

wherein the electrosurgical instrument is an electrosurgical forceps for sealing tissue, the forceps comprising:

at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and a sealing plate attached to each of the jaw members in opposing relation thereto, said sealing plates adapted to connect to the electrosurgical generator such that said sealing plates communicate electrosurgical energy through tissue held therebetween;

wherein a tissue impedance profile during an entire tissue sealing procedure varies in a non-linear manner, such that in a first phase the initial tissue impedance drops to reach a minimum impedance, in a second phase rises at a first rate, and in a third phase rises at a second rate, the second rate being less than the first rate and the second rate stabilizing over a period of time.

10. An electrosurgical generator as in claim 9, wherein the microprocessor is further adapted to adjust output of the electrosurgical generator based on the at least one tissue parameter.

11. An electrosurgical generator as in claim 9, wherein the at least one tissue treatment parameter is selected from the group consisting of pressure to be applied to tissue, duration of energy application, amount of energy to be supplied and target impedance trajectory.

12. An electrosurgical generator as in claim 9, wherein the electrosurgical generator is connected to an electrosurgical instrument including at least one active electrode adapted to apply electrosurgical energy to tissue.

13. An electrosurgical generator as in claim 9, wherein the constant value of the electrical signal is selected from the group consisting of constant voltage, constant current, constant power and constant energy.

* * * * *